United States Patent [19]

Enright

[11] Plant 4,775

[45] Oct. 13, 1981

[54] GAZANIA PLANT

[76] Inventor: Paul C. Enright, 11615 Riverside Dr., Lakeside, Calif. 92040

[21] Appl. No.: 173,183

[22] Filed: Jul. 28, 1980

[51] Int. Cl.[3] ..... A01H 5/00

[52] U.S. Cl. ..... Plt./68

[58] Field of Search ..... Plt./68

*Primary Examiner*—James R. Feyrer

[57] ABSTRACT

A new and distinct Gazania plant having flat, daisy flowers with typically 16 petals is disclosed. Each petal comprises a basal pattern of black to bronze to black with a white spot substantially centered between the basal black and bronze components. The remaining flower color progresses from deep orange to light orange near the tip, and fades with age.

1 Drawing Figure

The present invention relates to a new and distinct variety of Gazania plant, which I choose to name Magestic Sunset. This new and distinct variety of Gazania plant is characterized by its unique flower and varying leaf form.

The new and distinct variety was discovered as a seedling at my growing grounds, located in Lakeside, Calif., in a cultivated row of Super Fiesta Gazania, (an unpatented new variety of Gazania which has an orange flower with black and orange rayed stripes).

Asexual reproduction of the new and distinct variety has been accomplished by taking cuttings. Numerous cuttings have been made at my Lakeside, Calif. growing grounds and all of the resulting plants have exhibited the above-mentioned distinguishing characteristics which have been transmitted through succeeding propagations, thereby establishing that the strain is true.

The accompanying photographs in full color show the flower and foliage of the new and distinct variety of Gazania plant. These color photographs are as correct as it is possible to reproduce the color of the flower and foliage.

A detailed description of the new and distinct variety of Gazania plant follows. To facilitate identification of the important colors referred to in this specification, the color terminology adopted by the *Dictionary of Color* by Maerz and Paul has been adopted.

THE PLANT

Form: Ground cover type plant that is best described as clump.

Foliage:

*Quantity.*—Abundant.

*Shape.*—There are two distinct shapes of leaves. Both leaves have a 7 cm.–8 cm. linear base. The tip of one type is oblanceolate with apex acute, whereas the other type is parted near the tip with 2–5 partitions.

*Size.*—Full grown leaves are 15 cm.–16 cm. in length, with the oblanceolate-acute shaped leaves varying from 1 cm.–1.5 cm. at the widest portion, and the parted shaped leaves varying from 4 cm.–5 cm. at the widest portion.

*Ribs and veins.*—The veins are not prominent on either side of the leaf, while the central rib is very prominent on the underside of the leaf, and terminates at the apex as a sharp line.

*Texture.*—The leaves are rather thick. The underside has a sericeous covering, while the upperside is waxy.

*Color.*—The upperside of the leaf is Dark Green plate 24/L6. The underside of the leaf is White plate 9/A1, with the central rib being a Dull Green plate 22/H4.

*Leaf margins.*—Half of the leaves have margins that are entire, and the other half are parted near the tip.

THE FLOWER

Blooming habit: The new variety seems to bloom throughout the year in Southern California.

Buds:

*Size.*—Most buds are from 1 cm.–2 cm. in diameter.

*Form.*—Buds are campanulate in shape, from which a pointed tip emerges.

Flower:

*Size.*—The size of the bloom varies from 5 cm.–7 cm. in diameter.

*Form.*—The overall flower shape is flat daisy form, with the petals being ligulate in shape. A typical flower has 16 petals.

*Borne.*—Flowers are borne singly on a stem that can be up to 20 cm. in length.

*Color.*—The flower has three basal rings. The inner ring is black, the middle ring is Bronzesheen® plate 16/H12 with white spots, and the outer ring is black. The petals are Oxheart® plate 6/L5 near the outer basal ring, and fade to Orange Rufous® plate 11/L12 as they approach the tip. As the flower ages, its original color fades to a Sunflower Yellow plate 9/L4 near the tip.

*Petal shape.*—The petals are attenuate-obtuse in shape, measuring 3 cm.–4 cm. in length and are about 1.2 cm. at the widest portion.

I claim:

1. A new and distinct variety of Gazania plant substantially as herein described, characterized particularly as to novelty by its unique flower and varying leaf form.

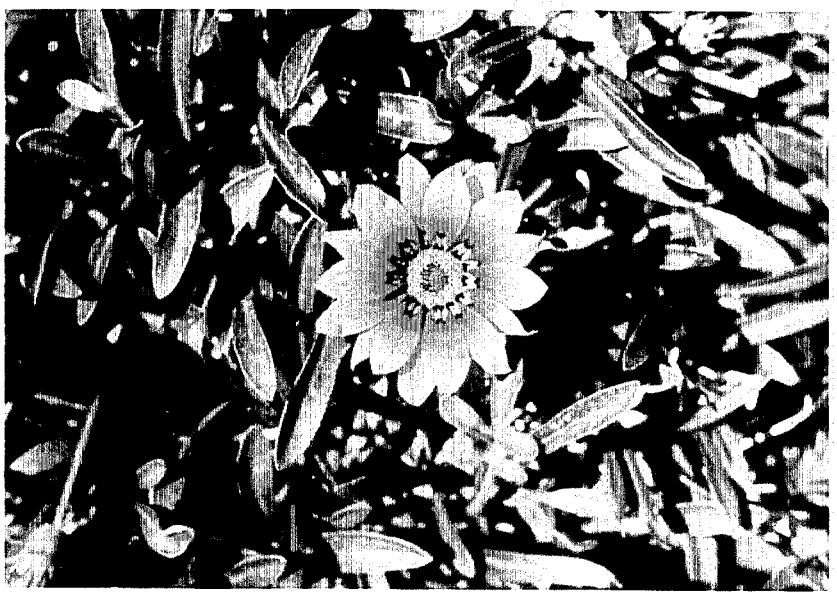

* * * * *